United States Patent [19]

Holmwood et al.

[11] Patent Number: 4,843,089
[45] Date of Patent: *Jun. 27, 1989

[54] ANTIMYCOTIC AGENT

[75] Inventors: Graham Holmwood; Wolfgang Krämer, both of Wuppertal; Karl H. Büchel, Burscheid; Manfred Plempel, Haan, all of Fed. Rep. of Germany

[73] Assignee: Bayer Aktiengesellschaft, Leverkusen, Fed. Rep. of Germany

[*] Notice: The portion of the term of this patent subsequent to Feb. 24, 2004, has been disclaimed.

[21] Appl. No.: 55,818

[22] Filed: May 29, 1987

Related U.S. Application Data

[63] Continuation of Ser. No. 778,347, Sep. 20, 1985, abandoned.

[30] Foreign Application Priority Data

Oct. 5, 1984 [DE] Fed. Rep. of Germany ....... 3436452

[51] Int. Cl.$^4$ .................. A61K 31/41; A61K 31/415
[52] U.S. Cl. ..................................... 514/383; 514/399
[58] Field of Search ............................... 514/383, 399

[56] References Cited

U.S. PATENT DOCUMENTS

| | | | |
|---|---|---|---|
| 3,890,442 | 6/1975 | Meiser et al. | 514/383 |
| 3,983,240 | 9/1976 | Buchel et al. | 514/383 |
| 4,406,909 | 9/1983 | Krämer et al. | 514/383 X |
| 4,427,673 | 1/1984 | Krämer et al. | 514/383 X |
| 4,645,767 | 2/1987 | Holmwood et al. | 514/383 |

OTHER PUBLICATIONS

Wolf et al, *The Fungi*, vol. II, John Wiley & Sons, pp. 365, 373 & 379 (1947).

*Primary Examiner*—Leonard Schenkman
*Attorney, Agent, or Firm*—Sprung, Horn Kramer & Woods

[57] ABSTRACT

A method of combating mycoses which comprises administering to a patient an antimycotically effective amount of a hydroxyethyl-azole of the formula

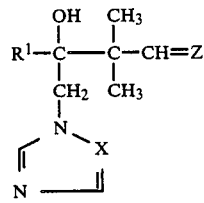

in which
  $R^1$ represents alkyl or the grouping Ar—Y—,
  Ar represents optionally substituted aryl,
  Y represents a direct bond or the groupings —$CH_2$—, —$CH_2$—$CH_2$—, —$OCH_2$—, —$SCH_2$—, —CH=CH— or —C≡C—,
  X represents a nitrogen atom or the CH group,
  Z represents oxygen or the $NOR^2$ group and
  $R^2$ represents hydrogen, alkyl, alkenyl, alkinyl, optionally substituted aralkyl or optionally substituted cycloalkylalkyl, or an acid addition salt thereof.

8 Claims, No Drawings

ANTIMYCOTIC AGENT

This is a continuation of application Ser. No. 778,347, filed Sept. 20, 1985, now abandoned.

The present invention relates to the use of hydroxyethyl-azole derivatives as antimicrobial agents, in particular as antimycotics.

It has been disclosed that certain 1-hydroxyethylazolyl derivatives have generally good antimycotic properties.

It has been found that the hydroxyethyl-azole derivatives of the general formula $$R^1-\underset{\underset{N\underset{\parallel}{\diagdown}\underset{X}{\diagup}}{\overset{|}{CH_2}}}{\overset{\overset{OH}{|}}{C}}-\underset{\overset{|}{CH_3}}{\overset{\overset{CH_3}{|}}{C}}-CH=Z \quad (I)$$

in which
  $R^1$ represents alkyl or the grouping Ar—Y—,
  Ar represents optionally substituted aryl,
  Y represents a direct bond or the groupings —CH$_2$—, —CH$_2$—CH$_2$—, —OCH$_2$—, —SCH$_2$—, —CH=CH— or —C≡C—,
  X represents a nitrogen atom or the CH group,
  Z represents oxygen or the NOR$^2$ group and
  R$^2$ represents hydrogen, alkyl, alkenyl, alkinyl, optionally substituted aralkyl or optionally substituted cycloalkylalkyl, and acid addition salts thereof, have good antimicrobial, in particular antimycotic, properties.

The compounds of the formula (I) have an asymmetric carbon atom and can therefore be obtained in the two optical isomer forms.

Surprisingly, the hydroxyethyl-azole derivatives of the formula (I) to be used according to the invention have a better action spectrum in certain fields of indication than the 1-hydroxyethyl-azolyl drivatives known from the prior art, such as 1-(4-chloro-phenoxy)-3,3-dimethyl-2-(imidazol-1-yl-methyl)-2-butanol and 1-(2-methylphenoxy)-3,3-dimethyl-2-(imidiazol-1-yl-methyl)-2-butanol, which are closely related compounds structurally and from the point of view of their action.

Formula (I) provides a general definition of the hydroxyethyl-azole derivatives according to the invention. Preferably, in this formula,
  $R^1$ represents straight-chain or branched alkyl with 1 to 6 carbon atoms or the grouping Ar—Y;
  Ar represents naphthyl, or phenyl which is optionally monosubstituted or polysubstituted by identical or different substituents, preferred substituents which may be mentioned being: halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, such as, preferably, fluorine and chlorine atoms, the —CH=NOR$^2$ radical, and phenyl, phenoxy, benzyl and benzyloxy, each of which is optionally substituted by halogen and/or alkyl with 1 or 2 carbon atoms;
  X represents a nitrogen atom or the CH group;
  Y represents a direct bond or the groupings —CH$_2$—, CH$_2$CH$_2$—, —OCH$_2$—, —SCH$_2$—, —CH=CH— or —C≡C—;
  Z represents oxygen or the NOR$^2$ group; and
  R$^2$ represents hydrogen, straight-chain or branched alkyl with 1 to 6 carbon atoms, alkenyl or alkinyl with in each case 2 to 6 carbon atoms, or phenylalkyl which has 1 to 2 carbon atoms in the alkyl part and is optionally monosubstituted or polysubstituted by identical or different substituents, possible substituents on the phenyl being the substituents on phenyl which have already been mentioned in the case of Ar; or represents cycloalkylmethyl which has 5 or 6 carbon atoms in the cycloalkyl part and is optionally mono-, di- or tri-substituted by identical or different alkyl radicals with 1 to 3 carbon atoms. Particularly preferred compounds of the formula (I) are those
in which
  $R^1$ represents straight-chain alkyl with 1 to 6 carbon atoms or the grouping Ar—Y—;
  Ar represents naphthyl, or represents phenyl which is optionally mono-, di- or tri-substituted by identical or different substituents, substituents which may be mentioned being: fluorine, chlorine, methyl, trifluormethyl, trifluoromethoxy, trifluoromethylthio, methoximinomethyl, ethoximinomethyl and allyloximinomethyl, and phenyl, phenoxy, benzyl and benzyloxy, each of which is optionally substituted by chlorine and/or methyl;
  X represents a nitrogen atom or the CH group;
  Y represents a direct bond or the groupings —CH$_2$—, —CH$_2$CH$_2$—, —OCH$_2$—, —SCH$_2$—, —CH=CH— or —C≡C—; and
  Z represents oxygen or the NOR$^2$ group,
wherein
  R$^2$ represents hydrogen, methyl, ethyl, n-propyl, n-butyl, allyl or propargyl, or represents benzyl which is optionally mono-, di- or tri-substituted by identical or different substituents from the group comprising fluorine, chlorine, methyl, trifluoromethyl and trifluoromethoxy, or represents cyclohexylmethyl which is optionally substituted by methyl or ethyl.

Addition products of acids and those hydroxyethylazole derivatives of the formula (I) in which the substituents R$^1$, X and Z have the meanings which have already been mentioned as preferred for thse substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulphonic acid and 1,5-naphthalenedisulphonic acid.

The hydroxyethyl-azole derivatives to be used according to the invention and their acid addition salts are the subject of U.S. application Ser. No. 650,965, filed Sept. 14, 1984, now pending, corresponding to German Patent Application P 3,334,779, and they can be obtained by a process in which (a) hydroxyethylazolyl acetal derivatives of the formula (II)

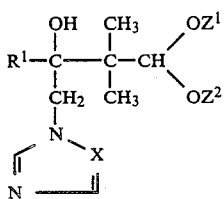

(II)

in which

Z$^1$ and Z$^2$ represent alkyl, or, together with the oxygen atoms to which they are bonded, represent a dioxolane ring; and R$^1$ and X have the abovementioned meanings, are reacted in the presence of a mixture of water and an organic solvent, such as, for example, alcohols, and in the presence of an acid, such as, for example, hydrochloric acid, at temperatures between 30° C. and 120° C.; or (b) the hydroxyethyl-azole derivatives obtained by process (a), of the formula (Ia)

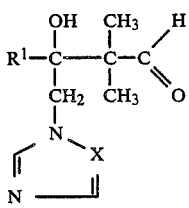

(Ia)

in which

R$^1$ and X have the abovementioned meanings, or the hydroxyethylazolyl acetal derivatives of the formula (II), are reacted with hydroxylamine derivatives of the formula (III)

 H$_2$N—O—R$^2$  (III)

in which

R$^2$ has the abovementioned meanings, in the presence of a diluent, such as, for example, alcohols and water, or mixtures of the two, at temperatures between 50° C. and 100° C.; or (c) the hydroxyethyl-azole derivatives obtained by process (b), of the formula (Ib) (that is to say those compounds of the formula (I) in which Z represents the NOH group)

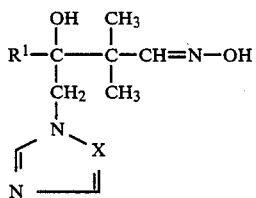

(Ib)

in which

R$^1$ and X have the abovementioned meanings, are reacted with halides of the formula (IV)

 Hal—R$^3$  (IV)

in which

Hal represents chlorine, bromine or iodine and

R$^3$ has the meanings of R$^2$, with the exception of hydrogen, in the presence of an inert organic solvent, such as, for example, dimethylsulphoxide, and if appropriate in the presence of a strong base, such as, for example, alkali metal hydrides or amides, at temperatures between 60° C. and 100° C.; or (d) oxiranes of the formula (V)

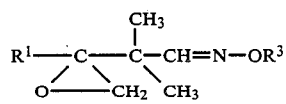

(V)

in which

R$^1$ and R$^3$ have the abovementioned meanings, are reacted with azoles of the formula (VI)

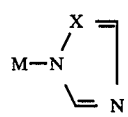

(VI)

in which

M represents hydrogen or an alkali metal, preferably sodium or potassium, in the presence of an inert organic solvent, such as, for example, alcohols or dimethylformamide, and if appropriate in the presence of a base, such as, for example, sodium alcoholate or potassium hydroxide, at temperatures between 60° C. and 150° C.

If appropriate, an acid can be added onto the compounds of the formula (I) thus obtained.

The hydroxyethylazolyl acetal derivatives of the formula (II) are known (compare DE-OS (German Published Specification) 3,242,222 and DE-OS (German Published Specification) 3,242,252); or they can be obtained by the process described therein, by a procedure in which oxiranes of the formula (VII)

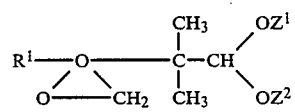

(VII)

in which

R$^1$, Z$^1$ and Z$^2$ have the abovementioned meanings, are reacted with azoles of the formula (VI) in the presence of an inert organic solvent, such as, for example, alcohols, and if appropriate in the presence of a base, such as, for example, a sodium alcoholate or potassium hydroxide, at temperatures between 60° C. and 150° C.

The oxiranes of the formula (VII) are known (compare DE-OS (German Published Specification) 3,242,252); or they can be obtained in a generally known manner, by a procedure in which ketones of the formula (VIII)

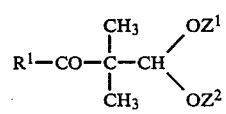

(VIII)

in which

R$^1$, Z$^1$ and Z$^2$ have the abovementioned meaning, either (α) are reacted with dimethyloxosulphonium methylide of the formula (IX)

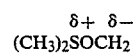

(IX)

in a manner which is known per se in the presence of a diluent, such as, for example, dimethylsulphoxide, at temperatures between 20° C. and 80° C. (in this context, compare the statements in J. Am. Chem. Soc. 87, 1363-1364 (1965)), or (β) are reacted with trimethylsulphonium methyl-sulphate of the formula (X)

$$[(CH_3)_3S^{(+)}] CH_3SO_4^{(-)} \quad (X)$$

in a manner which is known per se in the presence of an inert organic solvent, such as, for example, acetonitrile, and in the presence of a base, such as, for example, sodium methylate, at temperatures between 0° C. and 60° C., preferably at room temperature (compare also the statements in Heterocycles 8, 397 (1977)).

If appropriate, the resulting oxiranes of the formula (VII) can be further reacted directly, without being isolated.

The ketones of the formula (VIII) are known in some cases (compare, for example, J. Org. Chem. 32, 404 (1967); and DE-OS (German Published Specification) 3,224,130, DE-OS (German Published Specification) 3,224,129 and DE-OS (German Published Specification) 3,242,252); or they can be obtained in a known manner, for example by a procedure in which 1-(N-morpholino)-isobutene of the formula (XI)

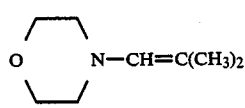

(XI)

is reacted with chlorides of the formula (XII)

$$R^1-CO-Cl \quad (XII)$$

in which

R¹ has the abovementioned meaning, in the presence of a solvent, such as, for example, diethyl ether, at temperatures between 20° C. and 120° C., and the keto derivatives thus obtained, of the formula (XIII)

(XIII)

in which

R¹ has the abovementioned meaning, are derivatized on the aldehyde group in the customary manner, such as, for example, by means of ethylene glycol in the presence of an inert organic solvent, such as, for example, toluene, and in the presence of a strong acid as the catalyst, such as, for example, p-toluenesulphonic acid, at temperatures between 80° C. and 110° C.

In some caes it proves to be advantageous to introduce the radical R¹ or components thereof only after the derivatization on the aldehyde group (compare also the preparation examples).

The hydroxylamine derivatives of the formula (III) are generally known compounds of organic chemistry.

The halides of the formula (IV) are generally known compounds of organic chemistry.

The oxiranes of the formula (V) can be obtained in a generally known manner, by a procedure in which keto-oxime derivatives of the formula (XIV)

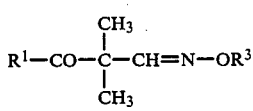

(XIV)

in which

R¹ and R³ have the abovementioned meanings, are epoxidized by processes (α) or (β) described above.

The keto-oxime derivatives of the formula (XIV) are known (compare DE-OS (German Published Specification) 3,224,130; DE-OS (German Published Specification) 3,224,129 and DE-OS (German Published Specification) 3,242,252); or they can be obtained in a known manner, for example by a procedure in which 1-(N-morpholino)-isobutene of the formula (XI) is reacted with chlorides of the formula (XII) in the presence of a solvent, such as, for example, diethyl ether, at temperatures between 20° C. and 120° C., and the keto derivatives thus obtained, of the formula (XIII), are derivatized on the aldehyde group in the customary manner by means of hydroxylamine derivatives of the formula (III), such as, for example, methoxyhydroxylamine hydrochloride, in the presence of an inert organic solvent, such as, for example, ethanol, and in the presence of sodium acetate, at temperatures between 80° C. and 110° C. In some cases, it proves advantageous to introduce the radical R¹ or parts thereof only after the derivatization of the aldehyde group.

The azoles of the formula (VI) are generally known compounds of organic chemistry.

The compounds of formula (I) can be converted into acid addition salts.

The acid addition salts of the compounds of the formula (I) can be obtained in a simple manner by customary salt formation methods, for example by dissolving a compound of the formula (I) in a suitable inert solvent and adding the acid, for example hydrochloride acid, and they can be isolated in a known manner, for example by filtration, and if appropriate purified by washing with an inert organic solvent.

The compounds of the formula (I) which can be used according to the invention, ester derivatives thereof and their acid addition salts display antimicrobial, in particular powerful antimycotic, actions. They have a very broad antimycotic action spectrum, in particular against dermatophytes and blastomyces, as well as biphase fungi, for example against Candida species, such as *Candida albicans*, Epidermophyton species, such as *Epidermophyton floccosum*, Asperigillus species, such as *Aspergillus niger* and *Aspergillus fumigatus*, Trichophyton species, such as *Trichophyton mentagrophytes*, Microsporon species, such as *Microsporon felineum*, and Torulopsis species, such as *Torulopsis glabrata*. The listing of these microorganisms in no way implies a limitation of the germs which can be combated, but is only of illustrative character.

Examples which may be mentioned of fields of indication in human medicine are: dermatomycoses and systemic mycoses caused by *Trichophyton mentagrophytes* and other *Trichlophyton* species, *Microsporon* species, *Epidermophyton floccosum*, blastomyces and biphase fungi as well as moulds.

Examples which may be mentioned of field of indication in vertinary medicine are: all dermatomycoses and systemic mycoses, in particular those caused by the abovementioned pathogens.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutically formulations in dosage units. This means that the formulations are in the form of individual parts, for example tablets, dragees, capsules, pills, suppositories and ampules, the active compound content of which corresponds to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amounts of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) distintegrating agents, for example agar-agar, calcium carbonate and sodium bicarbonate, (e) solution retarders, for example paraffin and (f) absorption accelerators, for example quaternary ammonium compounds (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifyiing agents, and can be of such a composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipitents, can also be in a microencapsulated form.

Suppositories can contain, in addition to the active compound or compounds, the customary water-soluble or water-insoluble excipients, for example polyethylene glycols, fats, for example cacao fat and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminium hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solution retarders and emulsifiers, for example water, ethyl alcohol, isopropyl alcohol, ethyl carbonate, ethyl acetate, benzyl alcohol, benzyl benzoate, propylene glycol, 1,3-butylne glycol, dimethylformamide, oils, in particular cottonseed oil, groundnut oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propyl alcohol, suspending agents, for example ethoxylated isostearyl alcohols, polyoxyethylene sorbitol and sorbitan ester, microcrystalline cellulose, aluminum methahydroxide, bentonite, agar-agar and tragacanth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5% by weight, preferably 0.5 to 95% by weight, of the total mixture.

The abovementioned pharmaceutical formulations can also contain other pharmaceutical active compounds, in addition to the active compounds according to the invention.

The abovementioned pharmaceutical formulations are prepared in the customary manner by known methods, for example by mixing the active compound or compounds with the excipient or excipients.

The present invention also includes the use of the active compounds according to the invention and of pharmaceutical formulations which contain one or more active compounds according to the invention, in human and veterinary medicine, for the prevention, alleviation and/or cure of the abovementioned diseases.

The active compounds or the pharmaceutical formulations can be administered locally, orally, parenterally, intraperitoneally and/or rectally, preferably parenterally, in particular intravenously.

In general, it has proved advantageous both in human medicine and in veterinary medicine to administer the active compound or compounds according to the invention in total amounts of about 2.5 to about 200 mg/kg, preferably 5 to 150 mg/kg, of body weight every 24 hours, if appropriate in the form of several individual administrations, in order to achieve the desired results.

In the case of oral administration, the active compounds according to the invention are administered in total amounts of about 2.5 to about 200 mg/kg, preferably 5 to 150 mg/kg, of body weight every 24 hours, and in the case or parenteral administraton, they are administered in total amounts of about 2.5 to about 50 mg/kg, preferably 1 to 25 mg/kg, of body weight every 24 hours.

However, it may be necessary to deviate from the dosages mentioned, and in particular to do so as a function of the species and body weight of the subject to be treated, the nature and severity of the disease, the type of formulation and of administration of the medicament and the period or interval within which adminitration takes place. Thus it can in some cases suffice to manage with less than the abovementioned amount of active compound, whilst in other cases the abovementioned amount of active compound must be exceeded. The particular optimum dosage required and the type of administration of the active compounds can easily be determined by anyone skilled in the art on the basis of his expert knowledge.

PREPARATION EXAMPLES

EXAMPLE 1

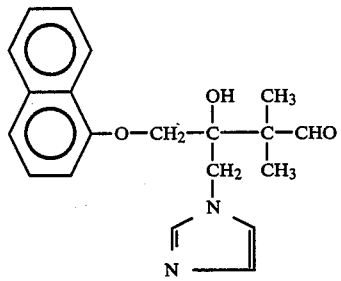

(Process a)

15 ml of concentrated hydrochloric acid are added to 22.7 g (0.059 mole) of 3-(1,3-dioxolan-2-yl)-2-(imidazol-1-yl-methyl)-3-methyl-1-(naphth-1-yl-oxy)-2-butanol in 150 ml of ethanol and 150 ml of water, and the mixture is heated under reflux for 4 hours. The reaction mixture is then poured into saturated aqueous sodium bicarbonate solution and extracted three times with methylene chloride. The combined organic phases are washed with water, dried over sodium sulphate and concentrated. The residue is taken up in ether/ethyl acetate and filtered off with suction.

17.0 g (85.3% of theory) of 2,2-dimethyl-3-hydroxy-3-(imidazol-1-yl-methyl)-4-(naphth-1-oxy)-butanal of melting point 147° C. are obtained.

Preparation of the starting substance

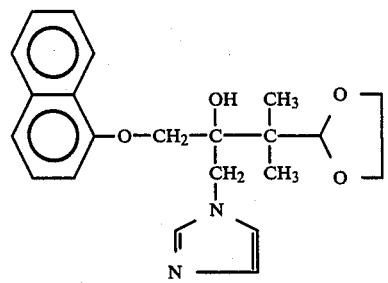

A solution of 53.5 g (0.17 mole) of 2-[2-(1,3-dioxolan-2-yl)-prop-2-yl]-2-(naphth-1-yl-oxymethyl)oxirane, 12.8 g (0.188 mole) of imidazole and 1.3 g of potassium hydroxide in 350 ml of absolute butanol is heated under reflux for 16 hours. The mixture is allowed to cool to room temperature and 500 ml of methylene chloride are added. The reaction mixture is washed twice with water. The organic phase is separated off, dried over sodium sulphate and concentrated. 350 ml of diisopropyl ether and ethyl acetate are added to the residue. The precipitate which has separated out is filtered off with suction.

38.3 g (59.4% of theory) of 3-(1,3-dioxolan-2-yl)-2-(imidazol-1-yl-methyl)-3-methyl-1-(naphth-1-yloxy)-2-butanol of melting point 126° C. are obtained.

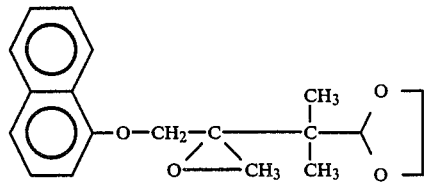

67.2 g (0.6 mole) of potassium tert.-butylate are added in portions to 131.1 g (0.596 mole) of trimethylsulphoxonium iodide in 120 ml of absolute dimethylformamide. The mixture is subsequently stirred at room temperature for 6 hours and a solution of 122 g (0.407 mole) of 2-(1,3-dioxolan-2-yl)-prop-2-yl naphth-1-yl-oxymethyl ketone in 550 ml of absolute tetrahydrofuran is then added. The reaction mixture is subsequently stirred overnight at room temperature and concentrated, the residue is taken up in methylene chloride and the mixture is washed twice with water, dried over sodium sulphate and concentrated. The residue is extracted by stirring in petroleum ether and is filtered off with suction.

107 g (83.7% of theory) of melting point 61° C. are obtained.

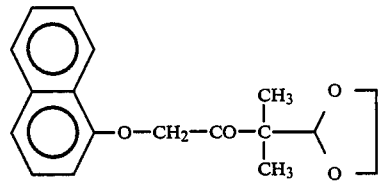

A solution of 141.5 g (0.735 mole) of 1-chloro-3-(1,3-dioxolan-2-yl)-3-methyl-2-butanone, 105.9 g (0.835 mole) of 1-naphthol and 122 g (0.882 mole) of potassium carbonate in 1,000 ml of absolute ethyl methyl ketone is heated under reflux for 16 hours. The mixture is allowed to cool to room temperature and is filtered. The filtrate is evaporated, methylene chloride is added to the residue and the mixture is washed once with dilute sodium hydroxide solution and twice with water, dried over sodium sulphate and concentrated. The residue is extracted by stirring in petroleum ether, filtered off with suction and dried.

122.6 g (55.6% of theory) of 2-(1,3-dioxolan-2-yl)-prop-2-yl naphth-1-yl-oxymethyl ketone of melting point 69° C. are obtained.

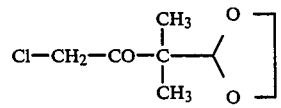

204 g (1.38 moles) of 4-chloro-2,2-dimethyl-3-keto-butanol are heated with 93 g (1.5 moles) of ethylene glycol and 0.7 g of p-toluenesulphonic acid in 400 ml of methylene chloride for 3 hours, using a water separator. The organic phase is extracted with 150 ml of 5% strength sodium hydroxide solution and then with 400 ml of water. The solvent is distilled off and the residue is distilled under a waterpump vacuum.

211 g (79.8% of theory) of 1-chloro-3-(1,3-dioxolan-2-yl)-3-methyl-butan-2-one of boiling points 127° C. to 128° C./14 mbar are obtained.

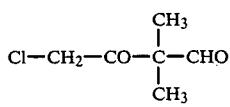

210 g (1.5 moles) of 1-(N-morpholino)-isobutene are added dropwise to 169 g (1.5 moles) of chloroacetyl chloride, dissolved and 350 ml of diethyl ether, at 5° C. in the course of one hour. When the addition has ended, the mixture is stirred under reflux for a further 3 hours. The solution is poured onto 100 g of ice, the pH is brought to 5 with aqueous sodium bicarbonate solution and the ether phase is separated off. The aqueous phase is extracted with 100 ml of diethyl ether and the organic phases are combined and dried over sodium sulphate, the solvent is distilled off and the residue is distilled under a waterpump vacuum.

EXAMPLE 2

136.4 g (61% of theory) of 4-chloro-2,2-dimethyl-3-keto-butanol of boiling point 95° C. to 98° C./14 mbar are obtained.

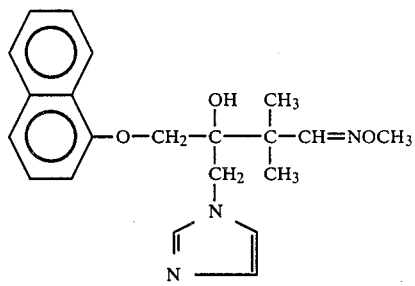

(Process b)

9 g (0.027 mole) of 2,2-dimethyl-3-hydroxy-3-(imidazol-1-yl-methyl)-4-(naphth-1-oxy)-butanol (Example 1) and 2.2 g (0.027 mole) of O-methyl-hydroxylamine hydrochloride are heated under reflux in 60 ml of ethanol for 16 hours. The reaction mixture is then concentrated and the residue is suspended in petroleum ether, filtered off with suction and dried.

9 g (90.7% of theory) of 2-(imidazol-1-yl-methyl)-3-methoxyiminomethyl-3-methyl-1-(naphth-1-oxy)-2-butanol of melting point 177° C. to 178° C. are obtained.

The following compounds of the general formula (I) are obtained in an analogous manner, corresponding to the process description according to the invention:

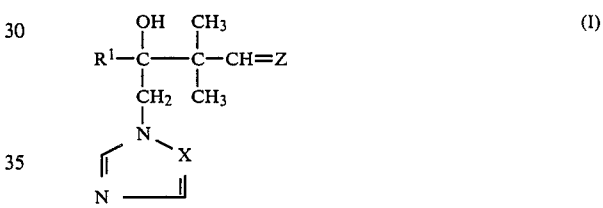

TABLE 1

| Example No. | $R^1$ | X | Z | Melting point (°C.) or spectroscopic data |
|---|---|---|---|---|
| 3 | Cl—⟨C6H4⟩—OCH2— | N | O | 107 |
| 4 | Cl—⟨C6H4⟩—OCH2— | N | NOCH3 | 144 |
| 5 | ⟨biphenyl⟩—OCH2— | N | O | Oil/IR$_{CHCl_3}$: CHO = 1720 cm$^{-1}$ |
| 6 | ⟨naphthyl⟩—OCH2 | N | O | Oil/IR$_{CHCl_3}$: CHO = 1722 cm$^{-1}$ |
| 7 | Cl—⟨C6H4⟩—CH2—CH2— | N | O | 105 |

TABLE 1-continued

| Example No. | R¹ | X | Z | Melting point (°C.) or spectroscopic data |
|---|---|---|---|---|
| 8 | 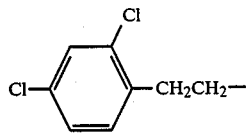 2,4-dichlorophenyl-CH₂CH₂— | N | O | 136 |
| 9 | 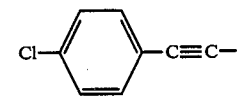 4-chlorophenyl-C≡C— | N | O | 119 |
| 10 | 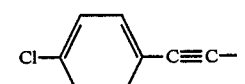 4-chlorophenyl-C≡C— | N | NOCH₃ | 121 |
| 11 | 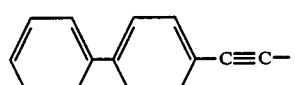 biphenyl-C≡C— | N | O | 147 |
| 12 | 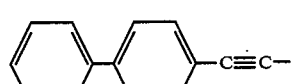 biphenyl-C≡C— | N | NOCH₃ | 151 |
| 13 | 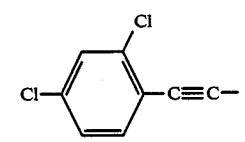 2,4-dichlorophenyl-C≡C— | N | NOCH₃ | 93 |
| 14 | 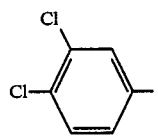 3,4-dichlorophenyl— | N | O | 147–151 |
| 15 | 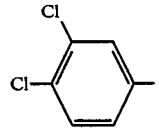 3,4-dichlorophenyl— | N | NOCH₃ | 96–101 |
| 16 | 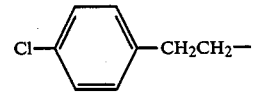 4-chlorophenyl-CH₂CH₂— | CH | O | 127 |
| 17 | 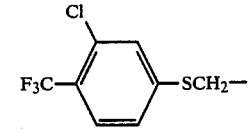 3-chloro-4-trifluoromethylphenyl-SCH₂— | N | NOCH₃ | Oil/¹H—NMR$_{CDCl_3}$: = 4.45 ppm for 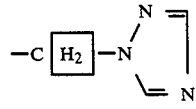 |
| 18 | 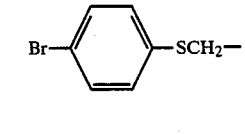 4-bromophenyl-SCH₂— | N | NOCH₃ | Oil/¹H—NMR$_{CDCl_3}$: = 4.42 ppm for 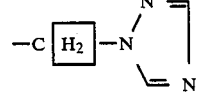 |
| 19 | 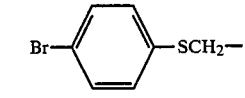 4-bromophenyl-SCH₂— | N | O | Oil/IR$_{CHCl_3}$: CHO = 1720 cm⁻¹ |

TABLE 1-continued
| Example No. | R¹ | X | Z | Melting point (°C.) or spectroscopic data |
|---|---|---|---|---|
| 20 | 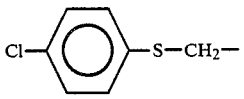 | CH | NOCH₃ | Oil/¹H—NMR$_{CDCl_3}$: = 4.13 ppm for 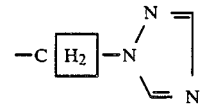 |
| 21 | 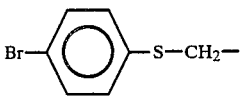 | CH | NOCH₃ | Oil/¹H—NMR$_{CDCl_3}$: = 4.15 ppm for 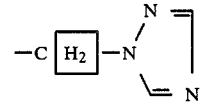 |
| 22 | 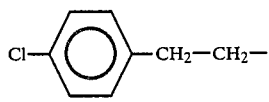 | N | NOCH₃ | Oil/¹H—NMR$_{CDCl_3}$: = 4.35 ppm for 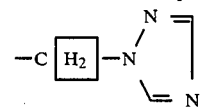 |
| 23 | 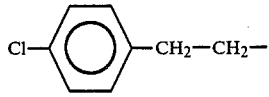 | N | NOC₄H₉ | Oil/¹H—NMR$_{CDCl_3}$: = 4.35 ppm for 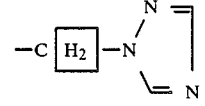 |
| 24 | 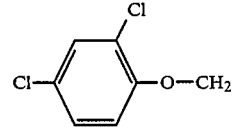 | N | NOCH₃ | 119 |
| 25 | 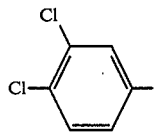 | N | NOC₂H₅ | 127–129 |
| 26 | 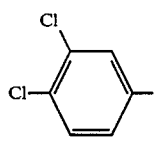 | N | NOC₄H₉—n | 138–140 |
| 27 | 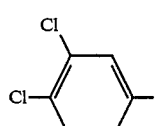 | N | NOCH₂—CH=CH₂ | 140–142 |
| 28 | 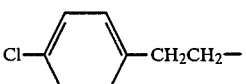 | N | 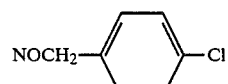 | 125–127 |
| 29 | 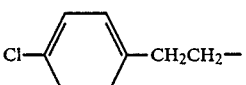 | N | 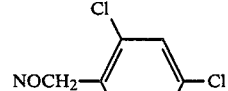 | 97 |
| 30 | 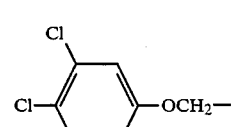 | N | 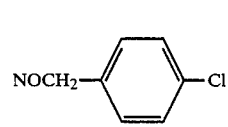 | 89–90 |

TABLE 1-continued
| Example No. | R¹ | X | Z | Melting point (°C.) or spectroscopic data |
|---|---|---|---|---|
| 31 | 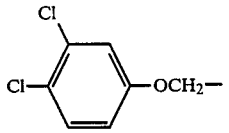 | N | 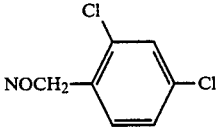 | 72 |
| 32 | 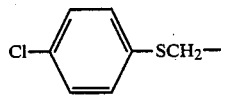 | N | NOCH₃ | viscous oil |
| 33 | 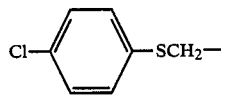 | N | NOCH₂—CH=CH₂ | 100–101 |
| 34 | CH₃ | N | 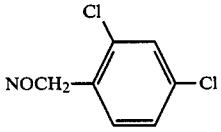 | viscous oil |
| 35 | 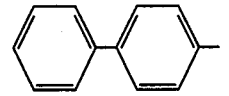 | N | NOCH₃ | 55–57 |
| 36 | 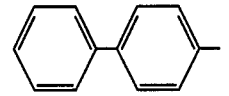 | N | NOCH₂—CH=CH₂ | 75 |
| 37 | 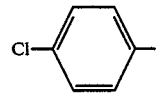 | N | NOCH₃ | 96–101 |
| 38 | 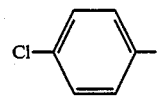 | N | NOC₃H₇—n | 112–114 |
| 39 | 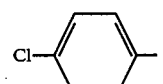 | N | 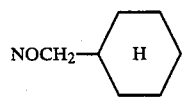 | 130–133 |
| 140 | 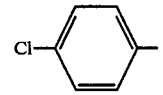 | N | NOC₄H₉—n | 124–130 |
| 41 | C₃H₇—n- | N | 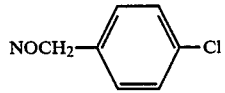 | viscous oil |
| 42 | C₃H₇—n- | N | 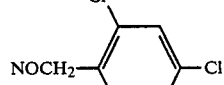 | viscous oil |

TABLE 1-continued

| Example No. | $R^1$ | X | Z | Melting point (°C.) or spectroscopic data |
|---|---|---|---|---|
| 43 | $C_2H_5-$ | N | NOCH$_2$-C$_6$H$_4$-Cl (4-Cl-phenyl) | $n_D^{20} = 1.5456$ |
| 44 | $C_2H_5-$ | N | NOCH$_2$-C$_6$H$_3$(Cl)$_2$ (2,4-dichlorophenyl) | viscous oil |
| 45 | $C_4H_9-n-$ | N | NOCH$_2$-cyclohexyl (H) | $n_D^{20} = 1.5021$ |
| 46 | $C_4H_9-n-$ | N | NOCH$_2$-C$_6$H$_4$-Cl (4-Cl-phenyl) | $n_D^{20} = 1.5353$ |
| 47 | $C_4H_9-n-$ | N | NOCH$_2$-C$_6$H$_3$(Cl)$_2$ (2,4-dichlorophenyl) | $n_D^{20} = 1.5438$ |
| 48 | $CH_3-(CH_2)_4-$ | N | NOCH$_3$ | 66–68 |
| 49 | $CH_3-(CH_2)_2-$ | N | NOCH$_3$ | 91 |
| 50 | $CH_3-(CH_2)_2-$ | N | NOC$_3$H$_7-$n | $n_D^{20} = 1.4886$ |
| 51 | $CH_3-(CH_2)_2-$ | N | NOCH$_2$-C$_6$H$_4$-CF$_3$ (4-CF$_3$-phenyl) | 54–57 |
| 52 | $CH_3-(CH_2)_4-$ | N | NOC$_3$H$_7-$n | $n_D^{20} = 1.4865$ |
| 53 | $CH_3-(CH_2)_4-$ | N | NOCH$_2-$CH$=$CH$_2$ | $n_D^{20} = 1.4949$ |
| 54 | $CH_3-(CH_2)_4-$ | N | NOCH$_2$-cyclohexyl (H) | $n_D^{20} = 1.4953$ |
| 55 | $CH_3-(CH_2)_4-$ | CH | NOCH$_2$-C$_6$H$_3$(Cl)(CF$_3$) | viscous oil |
| 56 | $CH_3-(CH_2)_4-$ | CH | NOCH$_2$-C$_6$H$_3$(Cl)(CF$_3$) | viscous oil |
| 57 | $CH_3-(CH_2)_4-$ | CH | NOCH$_2$-C$_6$H$_4$-CF$_3$ | viscous oil |
| 58 | $CH_3-(CH_2)_4-$ | CH | NOCH$_3$ | viscous oil |

TABLE 1-continued

| Example No. | R¹ | X | Z | Melting point (°C.) or spectroscopic data |
|---|---|---|---|---|
| 59 | 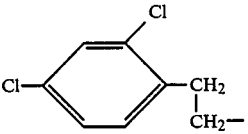 2,4-dichlorophenyl-CH₂CH₂- | N | NOCH₃ | viscous oil |
| 60 | 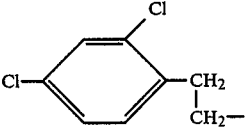 2,4-dichlorophenyl-CH₂CH₂- | N | NOC₂H₅ | viscous oil |
| 61 | 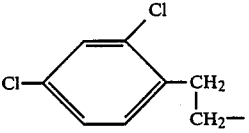 2,4-dichlorophenyl-CH₂CH₂- | N | NOC₃H₇—n | viscous oil |
| 62 | 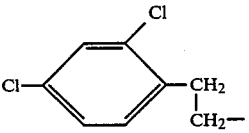 2,4-dichlorophenyl-CH₂CH₂- | N | NOCH₂—CH=CH₂ | viscous oil |
| 63 | 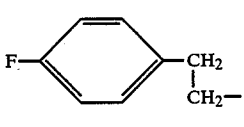 4-fluorophenyl-CH₂CH₂- | N | NOCH₃ | viscous oil |
| 64 | 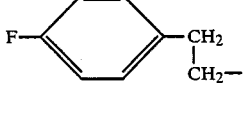 4-fluorophenyl-CH₂CH₂- | N | NOC₂H₅ | viscous oil |
| 65 | 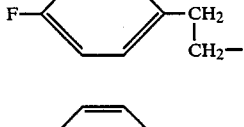 4-fluorophenyl-CH₂CH₂- | N | NOC₃H₇—n | viscous oil |
| 66 | 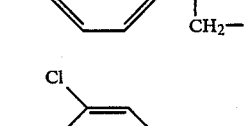 4-fluorophenyl-CH₂CH₂- | N | NOC₄H₉—n | viscous oil |
| 67 | 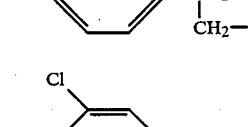 3,4-dichlorophenyl-CH₂CH₂- | N | NOCH₃ | 78–80 |
| 68 | 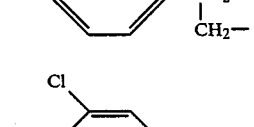 3,4-dichlorophenyl-CH₂CH₂- | N | NOC₃H₇—n | viscous oil |
| 69 | 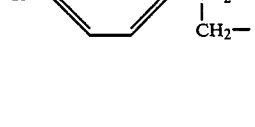 3,4-dichlorophenyl-CH₂CH₂- | N | NOC₄H₉—n | viscous oil |

TABLE 1-continued

| Example No. | R¹ | X | Z | Melting point (°C.) or spectroscopic data |
|---|---|---|---|---|
| 70 | 3,4-dichlorobenzyl-CH₂-CH₂- (Cl, Cl on phenyl; —CH(CH₂—)CH₂—) | N | NOCH₂—CH=CH₂ | viscous oil |
| 71 | CH₃—(CH₂)₃— | N | NOCH₃ | $n_D^{20} = 1.4940$ |
| 72 | CH₃—(CH₂)₃— | N | NOC₃H₇—n | $n_D^{20} = 1.4865$ |
| 73 | CH₃—(CH₂)₃— | N | NOCH₂—CH=CH₂ | 60–62 |
| 74 | CH₃—(CH₂)₃— | N | NOCH₂—C₆H₄—CF₃ | $n_D^{20} = 1.4974$ |
| 75 | CH₃—(CH₂)₃— | N | NOCH₂—C₆H₃(Cl)—CF₃ | $n_D^{20} = 1.5060$ |
| 76 | 4-Cl-2-F-phenyl- | N | NOCH₃ | 144 |
| 77 | 4-Cl-2-F-phenyl- | N | NOC₃H₇—n | 130–32 |
| 78 | 4-Cl-2-F-phenyl- | N | NOC₂H₅ | 134–37 |
| 79 | 4-Cl-2-F-phenyl- | N | NOC₄H₉—n | 144–46 |
| 80 | 4-Br-phenyl-S-CH(CH₂—)— | CH | NOC₃H₇—n | viscous oil |

USE EXAMPLES

The compounds shown below, which are known from DE-OS (German Published Specification) 3,018,865, are employed as comparison compounds in the use examples which follow:

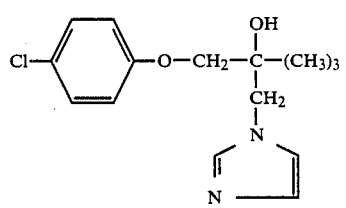
(A)

-continued

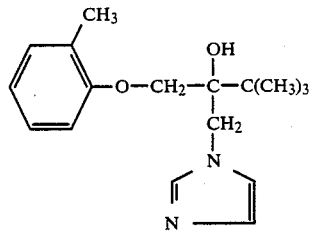
(B)

EXAMPLE A

Antimycotic in vitro activity

Description of the experiment

The in vitro tests were carried out in a series dilution test using germ inocular of on average $5\times 10^3$ to $10^4$ germs/ml of substrate. The nutrient medium used was (a) for dermatophytes and molds. Sabourand's milieu d'épreuve (b) for yeasts: meat extract/glucose broth.

The incubation temperature was 28° C. to 37° C. and the incubation period was 24 to 96 hours for yeasts and 96 hours for dermatophytes and molds.

In this test, for example, compounds 4, 7, 10, 11, 12, 13, 17, 18, 19, 20, 21, 22, 23, 28, 29, 30, 32, 33, 35, 36, 37, 38, 41, 42, 43, 45, 46 and 47 according to the invention exhibited a better antimycotic action than compound (B) known from the prior art.

TABLE A

Antimycotic in vitro activity
MIC values in /ml of nutrient medium

| Active compound | Tricho- phyton mentagr. | Micro- sporum canis | Candida albi- cans | Toro- lopsis glabrata | Asper- gillus fumigatus |
|---|---|---|---|---|---|
| (B) (known) | 32 | — | 32 | >64 | >64 |
| Compounds according to Preparation Example: | | | | | |
| 4 | <1 | 4 | <1 | 32 | 16 |
| 7 | <1 | 8 | 8 | 32 | 4 |
| 10 | <1 | 4 | 8 | 32 | 4 |
| 11 | <1 | <1 | 8 | 32 | 2 |
| 12 | <1 | 2 | <1 | 32 | 2 |
| 13 | <1 | 4 | 2 | 32 | 32 |
| 17 | <1 | 4 | 16 | 64 | 4 |
| 18 | <1 | 4 | 4 | 4 | 4 |
| 19 | <1 | 16 | 16 | 64 | 2 |
| 20 | <1 | 8 | <1 | <1 | 4 |
| 21 | <1 | 4 | <1 | <1 | 2 |
| 22 | <1 | <1 | 8 | 8 | <1 |
| 23 | <1 | 8 | 16 | 4 | 4 |
| 28 | <1 | 32 | <1 | 2 | 2 |
| 29 | <1 | 64 | <1 | 16 | 16 |
| 30 | <1 | 64 | 2 | 16 | 16 |
| 32 | <1 | 16 | <1 | <1 | 2 |
| 33 | <1 | 64 | <1 | <1 | 4 |
| 35 | <1 | 4 | <1 | 8 | 4 |
| 36 | <1 | 16 | 8 | 4 | 8 |
| 37 | <1 | 16 | <1 | 16 | 32 |
| 38 | <1 | 32 | <1 | 4 | 32 |
| 41 | <1 | 4 | 2 | 64 | 4 |
| 42 | 2 | 4 | 8 | 32 | 8 |
| 43 | <1 | 16 | 16 | 64 | 4 |
| 45 | 4 | 16 | <1 | 4 | 8 |
| 46 | 2 | 4 | <1 | 8 | 8 |
| 47 | 4 | 8 | <1 | 16 | 8 |

EXAMPLE B

Antimycotic in vivo activity (oral) on candidosis of mice

Description of the experiment

Mice of the SPF-CF$_1$ type were infected intravenously with $1-2\times 10^6$ logarithmically growing Candida cells suspended in physiological saline solution. The animals were treated orally with in each case 25–100 mg of the products/kg of body weight one hour before and seven hours after infection.

Result

Untreated animals died 3 to 6 days after infection. The survival rate on the 6th day after infection was about 5% in the untreated control animals.

In this test, for example, the compounds 4, 5, 8, 10, 12, 13, 16, 18, 20, 23, 24, 28, 32, 37, 38, 39 and 40 according to the invention exhibit a better action than compounds (A) and (B) known from the prior art.

Explanation of symbols

| | |
|---|---|
| + + + + + = very good action | = 90% of survivors on the 6th day after infection |
| + + + + = good action | = 80% of survivors on the 6th day after infection |
| + + + = action | = 60% of survivors on the 6th day after infection |
| + + = weak action | = 40% of survivors on the 6th day after infection |
| + = trace of action | = less than 40% of survivors on the 6th day after infection |
| n.a. = | = no difference to the untreated infection control |

TABLE B

Antimycotic in vivo action (oral) against candidosis of mice

| Active compound | Action |
|---|---|
| (A) (known) | n.a |
| (B) (known) | n.a. |
| Compounds according to Preparation Example: | |
| 4 | + + + + + |
| 5 | + + + + |
| 8 | + + + |
| 10 | + + + + + |
| 12 | + + + + |
| 13 | + + + |
| 16 | + + + + + |
| 18 | + + + + + |
| 20 | + + + + |
| 22 | + + + + + |
| 23 | + + + |
| 24 | + + + |
| 28 | + + + |
| 32 | + + + + + |
| 37 | + + + + + |
| 38 | + + + + + |
| 39 | + + + + |
| 40 | + + + + + |

EXAMPLE C

Antimicrobial in vivo activity (local) using the model of experimental trichophytosis in guinea pigs Description of the experiment White mice of the Pirbright-white strain were infected on their shaven, non-sacrificed backs with a microconidia and macroconidia suspension of Trichophyton von mentagrophytes.

The infected animals were treated locally, starting with the 3rd day after infection, 1× daily with a 0.1% strength solution of the products according to the invention (in dimethylsulphoxide: glycerol=1:4).

Result

The typical pattern of dermatophytosis with reddening, scaling and loss of hair up to total integumentary defect at the infection site developed on the untreated animals within 12 days after infection.

In this test, for example, compounds 18, 20, 22, 32, 37, 38 and 40 according to the invention show a good action.

TABLE C

Antimycotic in vivo activity (local) on the model of experimental trichophytosis in guinea pigs

| Active compound Compounds according to Preparation Example: | Action |
|---|---|
| 18 | +++ |
| 20 | +++ |
| 22 | +++ |
| 32 | ++++ |
| 37 | ++++ |
| 38 | ++++ |
| 40 | +++ |

Explanations:
+++++ = very good action = no signs of infection on the 12th to 15th day after infection
++++ = good action = slight redness, isolated scaling
+++ = action = redness, scaling without loss of hair
++ = weak action = redness, scaling, loss of hair
+ = trace of action = areas of loss of hair, inflammatory skin reaction

| Example/Formulations | |
|---|---|
| 1. Solution: | |
| Active compound according to formula (I) | 10 g |
| Alcohol, pure (96% strength) | 300 g |
| Isopropyl merisate | 526 g |
| | 836 g |
| 2. Cream: | |
| Active compound according to formula (I) | 10 g |
| Arlacel 60 (sorbitan monostearate) | 20 g |
| Tween 60 (polyoxyethylene(20) sorbitan monostearate) | 15 g |
| Spermaceti, synthetic (mixture of esters of saturated $C_{14}$-$C_{18}$-fatty acids and $C_{14}$-$C_{18}$-fatty alcohols) | 30 g |
| Lanette O (mixture of cetyl alcohol and stearyl alcohol) | 100 g |
| Etanol G (2-octyl-dodecanol) | 135 g |
| Benzyl alcohol | 10 g |
| Water, demineralized | 680 g |
| | 1,000 g |

It will be understood that the specification and examples are illustrative but not limitative of the present invention and that other embodiments within the spirit and scope of the invention will suggest themselves to those skilled in the art.

We claim:

1. A method of combating mycoses which comprises administering to a patient an antimycotically effective amount of a hydroxyethyl-azole of the formula $$R^1-\underset{\underset{CH_2}{|}}{\overset{\overset{OH}{|}}{C}}-\underset{\underset{CH_3}{|}}{\overset{\overset{CH_3}{|}}{C}}-CH=Z$$

in which
R¹ represents alkyl or the grouping Ar—Y—,
Ar represents aryl optionally substituted by halogen, alkyl with 1 to 4 carbon atoms, alkoxy or alkylthio with 1 or 2 carbon atoms, nitro, halogenoalkyl, halogenoalkoxy or halogenoalkylthio with 1 or 2 carbon atoms,
Y represents a direct bond or the groupings —CH₂—, —CH₂—CH₂—, —OCH₂—, —SCH₂—, —CH—CH— or —C=C—,
X represents a nitrogen atom or the CH group,
Z represents oxygen or the NOR² group and
R² represents hydrogen, alkyl, alkenyl, alkinyl, aralkyl optionally substituted by halogen, alkyl with 1 to 4 carbon atoms, alkoxy or alkylthio with 1 or 2 carbon atoms, nitro, halogenoalkyl, halogenoalkoxy or halogenoalkylthio with 1 or 2 carbon atoms, or $C_1$-$C_6$-cycloalkylmethyl optionally substituted by alkyl with up to 3 carbon atoms,
or an acid addition salt thereof.

2. The method according to claim 1, in which
R¹ represents straight-chain or branched alkyl with 1 to 6 carbon atoms or the grouping Ar—Y;
Ar represents naphthyl, or phenyl which is optionally substituted by halogen, alkyl with 1 to 4 carbon atoms, alkoxy or alkylthio with in each case 1 or 2 carbon atoms, nitro, halogenoalkyl, halogenoalkoxy or halogenoalkylthio with in each case 1 or 2 carbon atoms and 1 to 5 halogen atoms, the —CH—NOR² radical, and/or phenyl, phenoxy, benzyl or benzyloxy each of which is optionally substituted by halogen and/or alkyl with 1 or 2 carbon atoms; and
R² represents hydrogen, alkyl with 1 to 6 carbon atoms, alkenyl or alkinyl with in each case 2 to 6 carbon atoms, or phenylalkyl which has 1 or 2 carbon atoms in the alkyl part and is optionally substituted on the phenyl by the substituents which have already been mentioned in the case of Ar; or represents cycloalkylmethyl which has 5 or 6 carbon atoms in the cycloalkyl part and is optionally mono-, di- or tri-substituted by identical or different alkyl radicals with 1 to 3 carbon atoms.

3. The method according to claim 1, in which
R¹ represents straight-chain alkyl with 1 to 6 carbon atoms or the grouping Ar—Y—;
Ar represents naphthyl, or represents phenyl which is optionally mono-, di- or tri-substituted by fluorine, chlorine, methyl, trifluoromethyl, trifluoromethoxy, trifluoromethylthio, methoxyiminomethyl, ethoximinomethyl, allyloximinomethyl, and/or phenyl, phenoxy, benzyl or benzyloxy each of which is optionally substituted by chlorine and/or methyl; and R² represents hydrogen, methyl ethyl, n-propyl, n-butyl, allyl or propargyl, or represents benzyl which is optionally mono-, di- or tri-substituted by fluorine, chlorine, methyl, trifluoromethyl and/or trifluoromethoxy, or represents cyclohexylmethyl which is optionally substituted by methyl or ethyl.

4. The method according to claim 1, wherein such compound is of the formula

[Structure: 4-Br-C₆H₄-SCH₂-C(OH)(CH₂-triazolyl)-C(CH₃)(CH₃)-CH=NOCH₃]

or an acid addition salt thereof.

5. The method according to claim 1, wherein such compound is of the formula

[Structure: 4-Cl-C₆H₄-S-CH₂-C(OH)(triazolyl)-C(CH₃)(CH₃)-CH=NOCH₃]

or an acid addition salt thereof.

6. The method according to claim 1, wherein such compound is of the formula

[Structure: 4-Cl-C₆H₄-SCH₂-C(OH)(triazolyl)-C(CH₃)(CH₃)-CH=NOCH₃]

or an acid addition salt thereof.

7. The method according to claim 1, wherein such compound is of the formula

[Structure: 4-Cl-C₆H₄-C(OH)(triazolyl)-C(CH₃)(CH₃)-CH=NOCH₃]

or an acid addition salt thereof.

8. The method according to claim 1, wherein such compound is of the formula

[Structure: 4-Cl-C₆H₄-C(OH)(triazolyl)-C(CH₃)(CH₃)-CH=NOC₃H₇n]

or an acid addition salt thereof.

* * * * *